Figure 1:
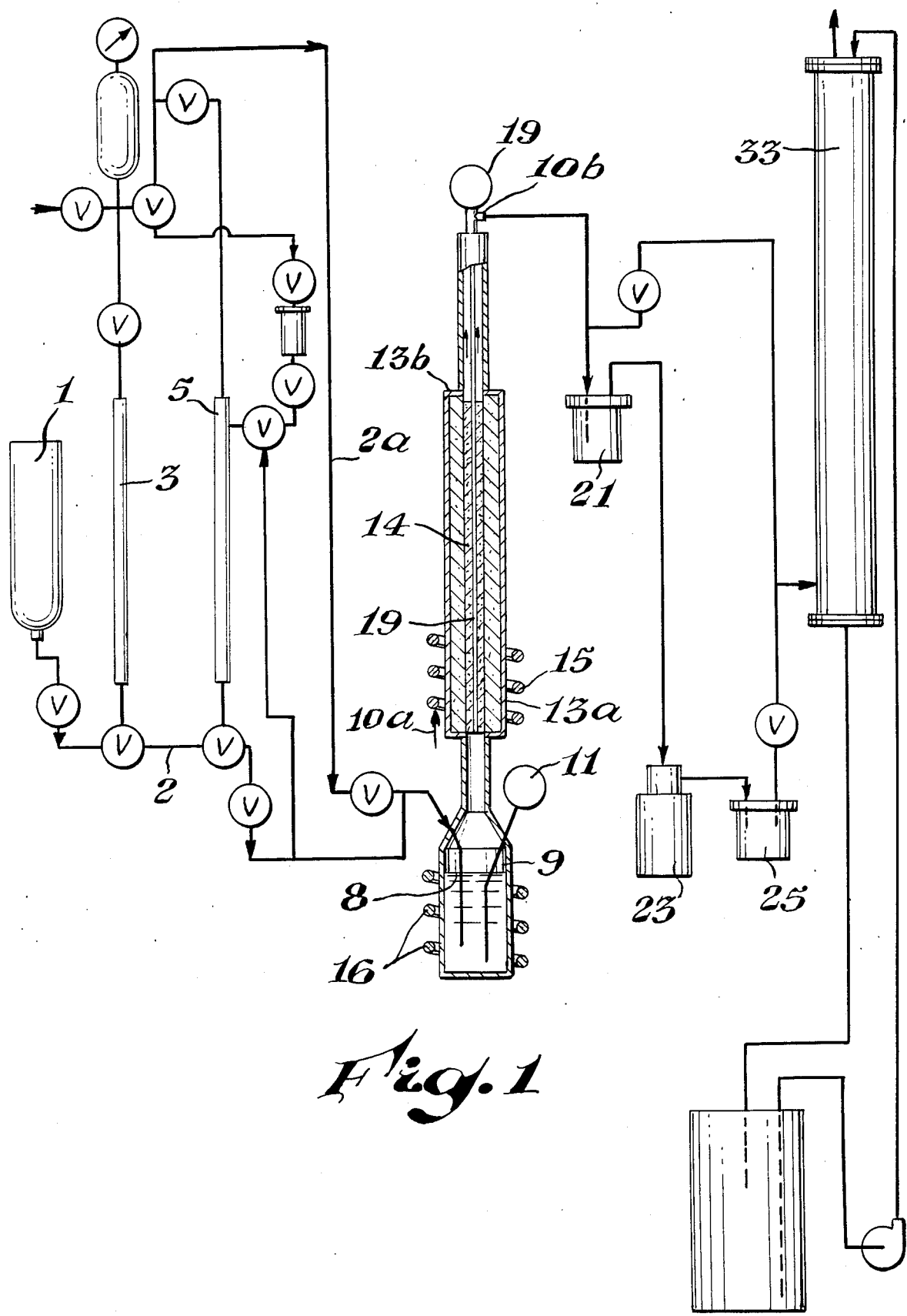

United States Patent [19]

Fujioka

[11] Patent Number: 4,680,406

[45] Date of Patent: Jul. 14, 1987

[54] PROCESS FOR FLUORINATING HALOGENATED ORGANO-COMPOUNDS

[75] Inventor: George S. Fujioka, Walnut Creek, Calif.

[73] Assignee: The Dow Chemical Company, Midland, Mich.

[21] Appl. No.: 787,190

[22] Filed: Oct. 15, 1985

[51] Int. Cl.$^4$ .................... C07D 211/72; C07C 17/20; C07C 19/08; C07C 21/24
[52] U.S. Cl. .................................. 546/345; 570/160; 570/165; 570/170; 570/175; 570/144; 570/145; 570/147; 558/425
[58] Field of Search ............... 546/345; 570/160, 165, 570/170, 175, 144, 145, 147; 558/425

[56] References Cited

U.S. PATENT DOCUMENTS 4,563,530  1/1986  Fujioka et al. ..................... 546/345

Primary Examiner—Henry R. Jiles
Assistant Examiner—Robert C. Whittenbaugh
Attorney, Agent, or Firm—Joseph T. Majka; Ronald G. Brookens

[57] ABSTRACT

A novel apparatus and a process for fluorinating organic compounds from halogen-containing organic compounds is disclosed.

5 Claims, 2 Drawing Figures

PROCESS FOR FLUORINATING HALOGENATED ORGANO-COMPOUNDS

FIELD OF THE INVENTION

The present invention relates to a novel apparatus and a novel process for fluorinating organic compounds derived from halogen-containing organic compounds.

BACKGROUND OF THE INVENTION

Fluorination is the process of adding fluoride to an organic compound employed as a feeder reactant. Apparatus and processes are known which utilize hydrogen fluoride (HF) in order to fluorinate organic feeder reactants to make fluoride-containing compounds. Such processes vaporize the HF and the feeder reactants to a temperature greater than the boiling point of either the HF or the feeder reactant and then pass the vaporized materials through a reactor containing a catalyst. The temperatures are constantly maintained above the boiling points of the HF and the feeder reactant, in order to prevent condensation during transit to and from the reactor. These known methods suffer the disadvantage that various organic feed reactants thermally decompose at temperatures greater than their boiling point. Further, upon decomposition, tars are formed which will deactivate or poison the catalyst. Such tars will cause blockage within the various chemical transport lines, forcing the chemical plant to shut down until the blockage is physically or chemically removed. Such shut down also causes lost production time, idle manpower, and a loss of overall efficiency of plant production. Also, decomposition of the feeder reactant will often result in a chemical product which is impure and of low yield. In many situations, the purity of the product may be so low that the chemical product must be discarded as hazardous waste, which has no known economical or beneficial applications. Furthermore, such methods also suffer the disadvantage of having high energy requirements necessary to effect the requisite volatilization.

Even in situations where the feeder reactants are stable at higher temperatures, such known processes still have serious disadvantages. For example, where heating within the transit lines or the reactor is uneven or inadequate, the feeder reactants can re-condense, liquify and deactivate the catalyst by filling or covering the surface of the pores within the catalyst. Deactivation is a deleterious process which reduces the inherent capacity of a catalyst to promote the conversion of one compound to another. Liquification of the feeder reactant on the catalyst will greatly reduce or eliminate the sites in the catalyst available for reaction through physical or chemical deactivation. The net effect of deactivation is that the catalyst life, yield and purity of the chemical product are adversely affected.

SUMMARY OF THE INVENTION

The present invention is directed to a novel apparatus of fluorinating compounds, comprising:
(a) a source of hydrogen fluoride;
(b) a vessel for holding a liquid pool of a feeder reactant;
(c) means for injecting said hydrogen fluoride from said source into said liquid pool and means for removing from said liquid pool a fraction of said aliphatic or aromatic reactant which is volatilized and mixed with said hydrogen fluoride;
(d) a catalyst bed communicating with said vessel to receive said mixture of reactant and hydrogen fluoride and to effect formation of a fluorine-containing compound;
(e) means for recovering the fluorine-containing compound from said catalyst bed.

The present invention is also directed to a novel process for preparing a fluorine-containing compound from a halogen-containing organic compound comprising:
(a) injecting hydrogen fluoride into a liquid pool of aliphatic or aromatic reactant containing at least one halogen which is not fluorine;
(b) removing a mixture from said liquid pool a fraction of said aliphatic or aromatic reactant which is volatilized and mixed with said hydrogen fluoride;
(c) passing said mixture of reactant and hydrogen fluoride over a catalyst bed to facilitate formation of a fluorine-containing compound; and
(d) recovering said fluorine-containing compound from said catalyst bed.

Fluorine-containing compounds have diverse commercial utility, and are used in making agricultural products such as herbicides and other pesticides.

The term "injecting" is used in its broadest sense as meaning to throw, drive, bubble or force the HF into the liquid pool of feed reactant.

The term "volatilize" is used in its generic sense as meaning to cause the aliphatic or aromatic reactant to pass off in vapor.

The term "hydrogen fluoride" is meant to mean the known compound of the formula HF. HF is a colorless, fuming, gas or liquid which is very soluble in water. HF can be prepared from the distillation of the reaction product of calcium fluoride and sulfuric acid.

The term "halogen" is employed herein to mean fluorine, chlorine, bromine and iodine.

The term "halogen-containing aliphatic reactant" is meant to include straight saturated, branched saturated or unsaturated hydrocarbons containing from 1 to 20 carbons, preferably four carbons and substituted by at least one halogen moiety, one of which is not flourine. Representative halogen-containing saturated aliphatic reactants include chloroethane, 1,2-dichloroethane, 1,5-dichloropentane, 1-fluoro-2,2-dichloroethane, 1-fluoro-5-chloropentane, 1-chlorocyclobutane and the like.

Representative halogen-containing unsaturated hydrocarbons include halogenated alkenes such as 1,2-dichloroethene, 3,3,3-trichloro-1-propene, 3,3-dichloro-1-propene, 3-bromo-3-chloro-1-propene, preferably 1,3-hexachlorobutadiene, perchloroethylene and hexachloropropene; and halogenated alkynes such as 3,3,3-trichloroprop-1-yne; and 3-bromo-3,3-dichloroprop-1-yne.

The term "halogen-containing aromatic reactant" is defined as an aromatic hydrocarbon or heterocyclic compound of the formula:

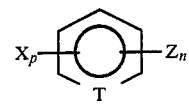

wherein
T is carbon or nitrogen,
X is halogen,
p is an integer from 0 to 6,

Z is a halogen-substituted aliphatic moiety or an aliphatic moiety which does not contain halogen, and n is an integer from 0 to 6 with the proviso $p+n \geq 1$ and either X or Z must contain at least one halogen which is not fluorine.

Aromatic reactants wherein T is carbon are known as substituted benzenes, wherein the benzene ring is substituted by either X, Z or both constituents, wherein X and Z are as defined hereinbefore. Such substituted benzenes include but are not limited to chlorobenzene, bromobenzene, 1,2-dichlorobenzene, 1,4-dichlorobenzene, 1-fluoro-2-chlorobenzene, 1-fluoro-4-chlorobenzene, 2-chloromethylbenzene, 2,4-dichloromethylbenzene, chloroethenylbenzene, 4-chlorobenzonitrile and the like, preferably 0-dichlorobenzene, 2,6-dichlorobenzonitrile, octachlorostyrene and hexachlorobenzene.

Aromatic reactants wherein T is nitrogen are known as substituted ptridines. Such pyridine reactants include 2-chloropyridine, 2-chloro-3-fluoropyridine, pentachloropyridine, 2,3-dichloro-5-trichloromethylpyridine and 2-chloro-5-trichloromethylpyridine.

The term "catalyst" designates a substance of which a fractional percentage notably affects the rate of a chemical reaction without itself being consumed or undergoing a chemical change. Carbon Catalysts, preferably those derived from carbon, include activated carbon catalysts, including carbons derived from plant materials, coal and petroleum sources. Particularly preferred carbon sources are those derived from coconut shell, for example the PCB-type catalysts from Pittsburgh Activated Carbon Co., Pittsburgh, Pa.

The catalysts of the present invention are intended to include those catalysts derived from carbon containing catalyst promotors which are supported on the carbon. Such catalyst promotors include metals from Group VIII of the periodic table such as the alkali metals of column IA including lithium (Li), sodium (Na), potassium (K), rubidium (Rb), cesium (Cs) and alkaline earth metals of column IIA including beryllium (Be), magnesium (Mg), calcium (Ca), strontium (Sr) and barium (Ba). Other catalytic promotors include metals from Row IV of the periodic table, including vanadium (V), chromium (Cr), manganese (Mn), iron (Fe), cobalt (Co), nickel (Ni), copper (Cu) and zinc (Zn), those from Row V such as ruthinium (Ru), rhodium (Rh), palladium (Pd), silver (Ag), tin (Sn) and those from Row VI such as tungsten (W), iridium (Ir), platinum (Pt) and lead (Pb).

The temperature at which the reaction mixture is passed over the catalyst can range from the temperature at which the feeder reactant exists as a liquid pool to about 550° C. Thus, the lower temperature limits are determined primarily by whether the feeder reactant is a liquid at a given temperature. The halogen containing aromatic or aliphatic compounds may be advantageously reacted with hydrogen flouride in the catalyst bed at temperatures as high as about 552° C., preferably from about 400° C. to about 500° C.

The resulting reaction mixture is usually maintained in contact with the catalyst for a period of time sufficient to provide for substantial completion of the reaction. Generally, the reaction is complete in a period from about 2 minutes to about 5 minutes, preferably in a time from about 20 seconds to about 40 seconds.

After the HF and the volatilized fraction of the aliphatic or aromatic reactant are removed from the liquid pool, the fluorination reaction in the catalyst bed can be carried out at sub-ambient, ambient or above ambient pressures, preferably at ambient pressures. Ambient pressure is usually about 15 pounds per square inch (psi). Sub-ambient pressures may range from about 1 psi to about 15 psi, whereas above-ambient pressures can be from more than 15 to about 200 psi.

A suitable molar ratio of reactants is from about 1:1 to about 100:1 (HF:halogen-containing aliphatic or aromatic compound) preferably in a molar ratio of about 3:1 to about 5:1.

IN THE DRAWINGS

In FIG. I is shown a cutaway of the fluorination unit used to prepare fluorine-containing compounds from halogen-containing compounds. The components of the fluorination unit are described as follows.

Hydrogen fluoride is withdrawn from inverted cylinder 1, a source of hydrogen fluoride, to a hydrogen fluoride-transfer reservoir 3 and from there transferred to hydrogen fluoride-feed reservoir 5. Transfers of the hydrogen fluoride gas through transfer lines 2 and 2a are usually made by relying upon the vapor pressure of the hydrogen fluoride to provide the force necessary for transfer. However, additional pressure by means of an inert gaseous source of pressure such as nitrogen pad 7 is available if necessary to effect the transfer. Ordinarily, nitrogen gas from nitrogen pad 7 is also used to purge the transfer lines and the catalyst bed 19a. Alternatively, nitrogen gas can be used as a carrier for hydrogen fluoride vapor to reactor 13. From the hydrogen fluoride-feed reservoir 5, hydrogen fluoride is injected by means of transfer lines 2 and 2a into feed evaporator 9, a vessel for holding a liquid pool of a feeder reactant. The aliphatic or aromatic reactants are designated as the "feed" or "feeder reactant".

The feed evaporator 9, made of nickel or any other inert material, provides 100 percent vapor feed to the reactor 13. The height of the liquid pool of aliphatic or aromatic reactant inside feed evaporator 9 is represented by level 8. Feed evaporator 9 is heated by heater 16. The temperature of the contents inside evaporator 9 are monitored and controlled by means of a thermocouple 11 communicating with feed evaporator 9. Means for removing from the liquid pool a fraction of said aliphatic or aromatic reactant which is volatilized and mixed with said hydrogen fluoride can be (a) pressure from HF, (b) and inert gaseous source of pressure, (c) means for manipulating pressures within reactor 13 or catalyst bed 14 or (d) any combination thereof in order to facilitate the removal.

Reactor 13, within which the catalyst bed 14 is located and the fluorine-containing compounds are prepared, is located atop feed evaporator 9. The catalyst bed 14 communitcates with feed evaporator 9 so as to receive the mixture of the reactant and the HF and effect formation of the desired fluorine-containing compound. Although the catalyst bed 14 is shown in the Figure to be situated vertically, the bed can be positioned in any manner relative to feed evaporator 9 to advantageously effect reaction upon said reactant feed and HF. Heat is supplied to reactor 13 by reactor heater 15. Reactor heater 15 can be a closely wound heating tape around reactor 13 or a coiled nichrome wire which is embedded in a ceramic shell. The temperature gradient along the length of the catalyst bed 14 within reactor 13 is monitored using a plurality of thermocouples 19 inside reactor 13. Volatile products of the fluorination reaction within reactor 13, emerge from the top 13b of reactor 13 and are directed through a series of traps 21, 23 and 25. Trap 21 serves as a means for recovering the fluorine-containing compounds from catalyst bed 14. Excess hydrogen fluoride gas which is not trapped by traps 21, 23 and 25 is passed into scrubber column 33 and removed as sodium fluoride (NaF) by liquid dilute caustic which is circulated within scrubber column 33.

Figure 2:
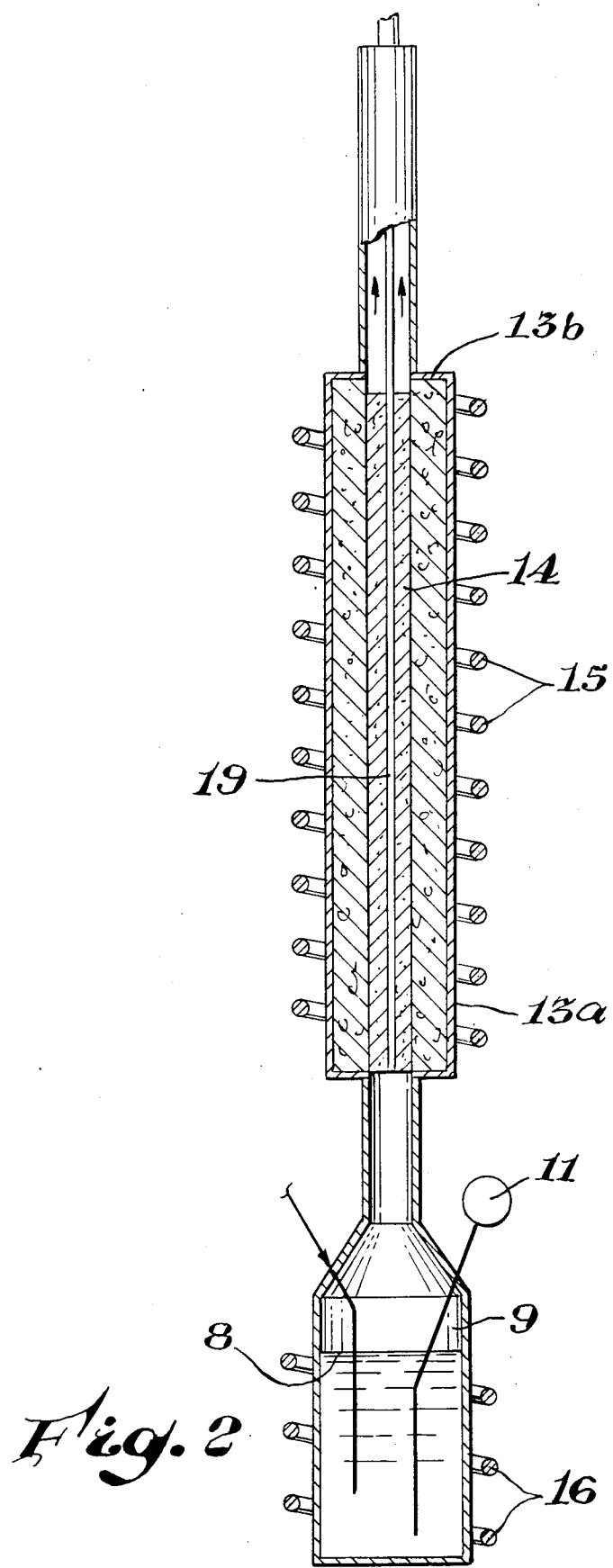

In FIG. 2 is shown a cutaway enlargement of the basic fluorination apparatus, including transfer lines 2 and 2a, feed evaporator 9, heater 16 for evaporator 9, reactor 13, catalyst bed 14, reactor heater 15, thermocouples 19 and top 13b of reactor 13.

Having described the components of the fluorination unit, the operation of the unit is described as follows. Catalyst bed 14 is heated to a temperature of up to about 500° C. with reactor heater 15. During operation, HF vapor is bubbled into the liquid pool of aliphatic or aromatic feed contained within feed evaporator 9 and becomes saturated with the feed vapors. The mixture of HF and a volatilized fraction of the feed vapors travel up in direction 10a into the catalyst bed 14 where reaction between HF and the feed vapors takes place. The catalyst bed 14 is highly porous and has a large surface area. HF and organic materials are strongly adsorbed on this surface. A small fraction of the carbon surface contain "active sites" where reaction can take place between HF and the feed reactant. The fluorinated organic product and hydrogen chloride by-products are desorbed from the surface of catalyst bed 14 and eventually exit the reactor 13 in direction 19a through top 13b into traps 21, 23 and 25. Trap 21 is specifically constructed to contain the desired fluorinated organic product.

The following examples are presented to illustrate preparation of typical compounds of the present invention, but the scope of the invention is not to be considered limited to the specific examples given.

EXAMPLE 1

Preparation of Fluorinated Pyridines from 2,3-Dichloro-5-trichloromethyl Pyridine A reactor unit was made from a 24 inch by ¾ inch diameter Hastelloy C pipe, threaded at both ends. Through a pipe fitting at the top of the reactir a ¼ inch diameter thermocouple well was dropped extruding axially to the bottom of the reactor. This well allowed the placement of as many as five separate thermocouples inside to monitor the temperature profile along the length of the catalyst bed. The thermocouple located mid-length of the catalyst bed was used for temperature control. Heat was supplied to the reactor by either a closely wound heating tape or by a coiled nichrome wire embedded-ceramic shell heater (Lindberg-Sola Basic Industries, Watertown, Wisc.). To the bottom of the reactor was attached a 300 ml nickel feed evaporator. The evaproator was heated by a 2¼ inch diameter by 1½ inch band heater (Chromalox-Emerson Electric Company, Pittsburgh, Pa.). Transfers of hydrogen fluoride gas to the feed evaporator were made using 100 ml hydrogen fluoride-transfer reservoirs and a 100 ml hydrogen fluoride feed reservoir. The reservoirs were made from ¾ inch outer diameter (O.D.) Teflon ®-PFA tubing and are sufficiently transluscent to discern the hydrogen fluoride liquid meniscus.

Anhydrous hydrogen fluoride was bubbled into a pool of 2,3-dichloro-5-trichloromethylpyridine which was heated to a temperature between 194°–204° C. The HF and the vapor of the 2,3-dichloro-5-trichloromethylpyridine were carried up into the catalyst bed which was heated to a temperature of 247° C. The average residence time of the reactants within the catalyst bed was 9 seconds. The molar ratios of hydrogen fluoride and 2,3-dichloro-5-trichloromethylpyridine was 3.6:1 (HF:2,3-dichloro-5-trichloromethyl pyridine). The products of the reaction were distilled out of the reactor and condensed in the product reservoir. Gas chromatography analysis on an area percent basis showed that of the 100.5 grams of product collected, 449 mmoles of halogenated pyridines were present, of the following product analysis:

| | |
|---|---|
| 2,3-difluoro-5-trifluoromethyl pyridine | 0.09% |
| 2-fluoro-3-chloro-5-trifluoromethyl pyridine | 12.80% |
| 2-fluoro-3-chloro-5-difluorochloromethyl pyridine | 0.20% |
| 2,3-dichloro-5-(?)trifluoromethyl pyridine | 72.40% |
| 2,3-dichloro-5-difluorochloromethyl pyridine | 12.90% |
| 2,3-dichloro-5-dichloro-fluoromethyl pyridine | 0.50% |

EXAMPLE 2

Preparation of Fluorinated Pyridines from Pentachloropyridine

With the apparatus as described in Example 1, 278 grams of pentachloropyridine (1108 mmoles) was placed into a 300 ml nickel reservoir. The reservoir was attached directly to a reactor containing 54 grams of dry coconut shell carbon, PCB-type (Pittsburgh Activated Carbon Company, Pittsburgh, Pa.). After the pentachloropyridine was heated to a temperature of 200° C., then hydrogen fluoride vapors were brought in below the surface of the molten pentachloropyridine. The reactor was heated to a temperature of 520° C. where fluorination produced halogen exchanged reactions. Products of the reaction were carried out of the reactor and condensed and collected in the product reservoirs outside of the reactors. Gas chromatic analysis on an area percent basis of the crude product collected in the product reservoirs showed that of the 261 grams of crude product collected, 177 grams was organic material. Of the organic material, the degree of fluorine for chlorine substitution was as follows:

| | |
|---|---|
| tetrafluoro | 0.3% |
| trifluoro | 9.2% |
| difluoro | 45.8% |
| monofluoro | 37.5% |
| chloro(starting material) | 7.2% |
| Total | 100.0% |

Fluorine-nuclear magnetic resonance (F-NMR) analysis showed the isomer distribution of the above fluorinated fractions to be as follows:

| | |
|---|---|
| trifluorinated pyridines | |
| 3,5-dichloro-2,4,6-trifluoropyridine | 62% |
| 3,4-dichloro-2,5,6-trifluoropyridine | 32% |
| 2 unresolved isomers | 6% |
| difluorinated pyridines | |
| 3,4,5-trifluoro-2,6-difluoropyridine | 72% |
| 2,3,5-trichloro-4,6-difluoropyridine | 17% |
| 2,4,5-trichloro-3,6-difluoropyridine | 7% |
| 2,3,4-trichloro-5,6-difluoropyridine | 4% |
| monofluorinated pyridines | |
| 2,3,4,5-tetrachloro-6-monofluoropyridine | 88% |
| 2,3,4,6-tetrachloro-5-monofluoropyridine | 6% |

| 2,3,5,6-tetrachloro-4-monofluoropyridine | 6% |

EXAMPLE 3

Preparation of Fluorinated Benzenes from O-dichlorobenzene

With the apparatus for fluorinating the compounds as described in Example 1, 64.6 g of anhydrous hydrogen fluoride (3231 mmoles) was bubbled into 50 ml of O-dichlorobenzene (65.8 grams or 439 mmoles) heated to a temperature of 114° C. The vapors of hydrogen fluoride/O-dichlorobenzene were sent to a catalyst containing 70 grams of activated coconut shell carbon heated to a temperature of 456° C. The average residence time was 14 seconds. In the product reservoir was collected 32.4 grams of liquid product. A gas chromatographic analysis of the liquid products showed this composition to contain the following:

| O—chloro-fluorobenzene | 7.9 |
| dichlorobenzenes (and mixed isomers from impurities in the starting materials) | 2.4 |
| O—dichlorobenzene | 89.6 |

EXAMPLE 4

Preparation of Fluorinated Benzonitriles from 2,6-Dichlorobenzonitrile

To the apparatus described as in Example 1, 70 g of anhydrous hydrogen fluoride (3522 mmoles) was bubbled into 25.2 of 2,6-dichlorobenzonitrile (B.P. 143°–146° C.) heated to a temperature of 166° C. Mixed vapors of hydrogen fluoride and 2,6-dichlorobenzonitrile were sent to a catalyst bed containing 77 grams of activated coconut shell carbon heated to a temperature of 529° C. The average residence time of the reactants in the catalyst bed was 30 seconds. The average ratio of hydrogen fluoride 2,6-dichlorobenzonitrile was determined to be 24:1 (HF:2,6-dichlorobenzonitrile). From the product reservoir was collected 3.4 grams of liquid product. Gas chromatographic analysis of the products showed the liquid product to be of the following composition:

| 2,6-difluorobenzonitrile | 82.5 |
| 2-chloro-6-fluorobenzonitrile | 6.6 |

EXAMPLE 5

Preparation of Fluorinated Styrene from Octachlorostyrene

To the apparatus described as in Example 1, anhydrous hydrogen fluoride (34 g) was bubbled into 100 grams of octachlorostyrene (M.P. 94°–96° C.) heated to a temperature between 245° C.–290° C. The mixed vapors of hydrogen fluoride/octachlorostyrene were sent to a catalyst bed containing 83.7 grams of coconut shell carbon catalyst heated to a temperature of 483° C. The average residence time was varied to seconds. The average hydrogen/fluoride octachlorostyrene mole ratio was 45:1 (HF:octachlorostyrene) in the product reservoir as recovered 11.5 grams of liquid product, whose gas chromatographic analysis showed a complex mixture:

| fluorinated styrenes | | 38.9% |
| fluorinated ethylbenzene | | 40–50% |
| fluorinated toluenes | | 1.8% |
| unresolved compounds | approximately | 20.0% |

EXAMPLE 6

Preparation of Fluoroethanes from Perchloroethylene

To the apparatus described as in Example 1, 80.1 g of anhydrous hydrogen fluoride, (4007 mmoles) was bubbled into 162.8 g perchloroethylene (982 mmoles) heated to 74° C. The mixed vapors were sent to a catalyst bed containing 60.6 g of activated coconut shell carbon heated to 422° C. The average residence time was 9 seconds. The average HF:C$_2$Cl$_4$ mole ratio was 13:1. The liquid product weighed 51.4 g. Gas chromatographic analysis of the products, on an area percentage basis, gave:

| 1,1,1-trichloro-2,2,2-trifluoroethane | 7.3% |
| 1,1,2-trichloro-2-fluoroethene | 9.4% |
| 1,1,1,2-tetrachloro-2,2-difluoroethane | 2.1% |
| perchloroethylene | 79.2% |

EXAMPLE 7

Preparation of Fluorinated Butadienes from 1,3-Hexachlorobutadiene

To an apparatus described as in Example 1, 85g of anhydrous hydrogen fluoride (4300 mmoles) was bubbled into 102 g of 1,3-hexachlorobutadiene (390 mmoles) heated to 150° C. The mixed vapors were sent to the catalyst bed containing 61 grams of activated coconut shell carbon heated to 350° C. The average residence time was 17 sec. The average HF:butadiene mole ratio was 11:1. The recovered liquid products weighed 38 g. Gas chromatographic analyses of the product, on an area percentage basis, identified by the number Cl-F exchange is given below:

| F$_4$Cl$_2$ | butadiene | 1.7% |
| F$_3$Cl$_3$ | butadiene | 1.7% |
| F$_2$Cl$_4$ | butadiene | 3.6% |
| FCl$_5$ | butadiene | 8.2% |
| Cl$_6$ | butadiene (starting material) | 71.7% |

EXAMPLE 8

Preparation of Fluorinated Propenes from Hexachloropropene

To an apparatus described as in Example 1, 57 g of anhydrous hydrogen fluoride, (2850 mmoles) was bubbled into 100 g hexachloropropene (385 mmoles), heated to 139° C. The mixed vapors were sent to a catalyst bed containing 61 g of activated coconut shell carbon heated to 430° C. The average residence time was 8 sec; the average HF:propene mole ratio was 7:1. The recovered liquid products weighed 22 g. Gas chromatographic analyses of the product on an area percentage basis was:

| hexafluorodichlorobutene | 3.1% |

-continued

|   |   |
|---|---|
| pentafluorotrichloropropane | 7.9% |
| tetrafluorodichloropropene | 4.1% |
| trifluorotrichloropropene | 52.6% |
| hexachloropropene (starting material) | 28.8% |

EXAMPLE 9

Preparation of Fluorinated Benzenes from Hexachlorobenzene

To an apparatus described as in Example 1, 17 g of anhydrous hydrogen fluoride (850 mmoles) was mixed with 42 grams hexachlorobenzene (147 mmoles) at 245° C. The mixed vapors were sent to a catalyst bed containing 60.7 g of activated coconut shell carbon heated to 498° C. The average residence time was 44 seconds; the average HF:$C_6Cl_6$ mole ratio was 6:1. The liquid products weighed 1.3 g. Gas chromatographic analysis of the products by number of F:Cl exchanges based on an area percentage basis gave:

|   |   |
|---|---|
| tetrafluorodichlorobenzene | 2.4% |
| trifluorotrichlorobenzene | 31.1% |
| difluorotetrachlorobenzene | 35.3% |
| monofluoropentachlorobenzene | 4.3% |
| unreacted hexachlorobenzene | 0.8% |

I claim:

1. A process for preparing a fluorine-containing compound from a halogen-containing organic compound comprising:
   (a) injecting hydrogen fluoride into a liquid pool of aliphatic or aromatic reactant containing at least one halogen which is not fluorine,
   (b) removing from said liquid pool a volatilized mixture of said aliphatic or aromatic reactant and hydrogen fluoride;
   (c) passing said mixture of reactant and hydrogen fluoride over a catalyst bed to facilitate formation of a fluorine-containing compound; and
   (d) recovering said fluorine-containing compound from said catalyst bed.

2. The process of claim 1 wherein the injection is performed by bubbling the hydrogen fluoride into the liquid pool.

3. The process of claim 1 wherein the aliphatic reactant is perchloroethylene, 1,3-hexachlorobutadiene or hexachloropropene.

4. The process of claim 1 wherein the aromatic reactant is 2,3-dichloro-5-trichloromethyl pyridine, pentachloropyridine, O-dichlorobenzene, 2,6-dichlorobenzonitrile, octachlorostyrene or hexachlorobenzene.

5. The method of claim 1 wherein said catalyst bed is derived from carbon.

* * * * *